United States Patent
Sano

[19]

[11] Patent Number: 6,080,038
[45] Date of Patent: Jun. 27, 2000

[54] PANTY GIRDLE

[76] Inventor: Michiko Sano, 50, Doki-cho Higashi 8-chome, Marugame-shi, Kagawa-ken, Japan

[21] Appl. No.: 09/374,094

[22] Filed: Aug. 12, 1999

[30] Foreign Application Priority Data

Aug. 26, 1998 [JP] Japan .................................. 10-239771
May 26, 1999 [JP] Japan .................................. 11-145847

[51] Int. Cl.$^7$ ................................................. A41C 1/08
[52] U.S. Cl. .......................... 450/155; 450/132; 602/19; 2/44; 128/100.1
[58] Field of Search ................................. 450/155, 132, 450/5–131; 602/29, 60, 61, 67; 2/44, 73, 92, 400–408, 338, 310–312, 236, 237; 604/393, 394, 397–402; 128/95.1, 96.1, 99.1, 100.1, 101.1

[56] References Cited

U.S. PATENT DOCUMENTS

| | | | |
|---|---|---|---|
| 1,185,672 | 6/1916 | Huettner | 450/155 |
| 1,391,563 | 9/1921 | Monin | 450/155 |
| 2,584,279 | 2/1952 | McDowell | 450/155 |
| 3,339,554 | 9/1967 | Nobbs | 450/132 |
| 3,431,913 | 3/1969 | Bugnon et al. | 450/132 |
| 4,697,592 | 10/1987 | Maddux et al. | 450/155 |
| 5,536,246 | 7/1996 | Saunders | 602/19 |
| 5,613,893 | 3/1997 | Zagame | 450/155 |

FOREIGN PATENT DOCUMENTS

4-21764  5/1992  Japan .

*Primary Examiner*—Gloria M. Hale
*Attorney, Agent, or Firm*—Graham & James LLP

[57] ABSTRACT

A panty girdle comprises an upper panty portion and lower thigh covering portions. An elastic belt is wholly or partially sewn to the inner circumferential surface of the panty portion of the panty girdle and extends downwards towards the middle of front panels of the panty girdle. When one wears the panty girdle, one's Iliums are tightened by connecting the ends of the belt to achieve pelvis correction.

11 Claims, 10 Drawing Sheets

PANTY GIRDLE

BACKGROUND OF THE INVENTION

The present invention relates to a panty girdle which provides pelvis correction.

In a known panty girdle, the opened pelvis is corrected or closed by tightening an upper portion of the iliums.

The right and left iliums in the pelvis do not rotate around a vertical axis which extends from the spinal column, but rotates around an inclined axis at connection of the iliums with the socrum.

A known panty girdle which provides pelvis correction tightens the upper part of the right and left iliums in a horizontal direction, so that a gap occurs between its tightening direction and original rotating direction of the iliums to cause stress to the connection between the iliums and the socrum or other bones to lead disadvantage to pelvis correction.

In a panty girdle which has no means for adjusting waist size, when a wearer has larger thigh than waist, if waist size of the panty girdle is fitted to thigh size, waist size will become loosened not to act pelvis correction, while the lower back of a wearer is likely to be much tightened when the wearer has larger waist size than thigh size.

SUMMARY OF THE INVENTION

In view of the disadvantages in the prior art, it is an object of the present invention to provide a panty girdle by which right and left iliums in a pelvis are tightened in an original rotational direction to obtain normal pelvis correction.

It is another object of the present invention to provide a panty girdle which can remove loosening of muscles in the lower back and adjust waist size.

BRIEF DESCRIPTION OF THE DRAWINGS

The features and advantages of the invention will become more apparent from the following description with respect to embodiments as shown in appended drawings wherein.

DETAILED DESCRIPTION OF PREFERRED EMBODIMENTS

Figure 1:
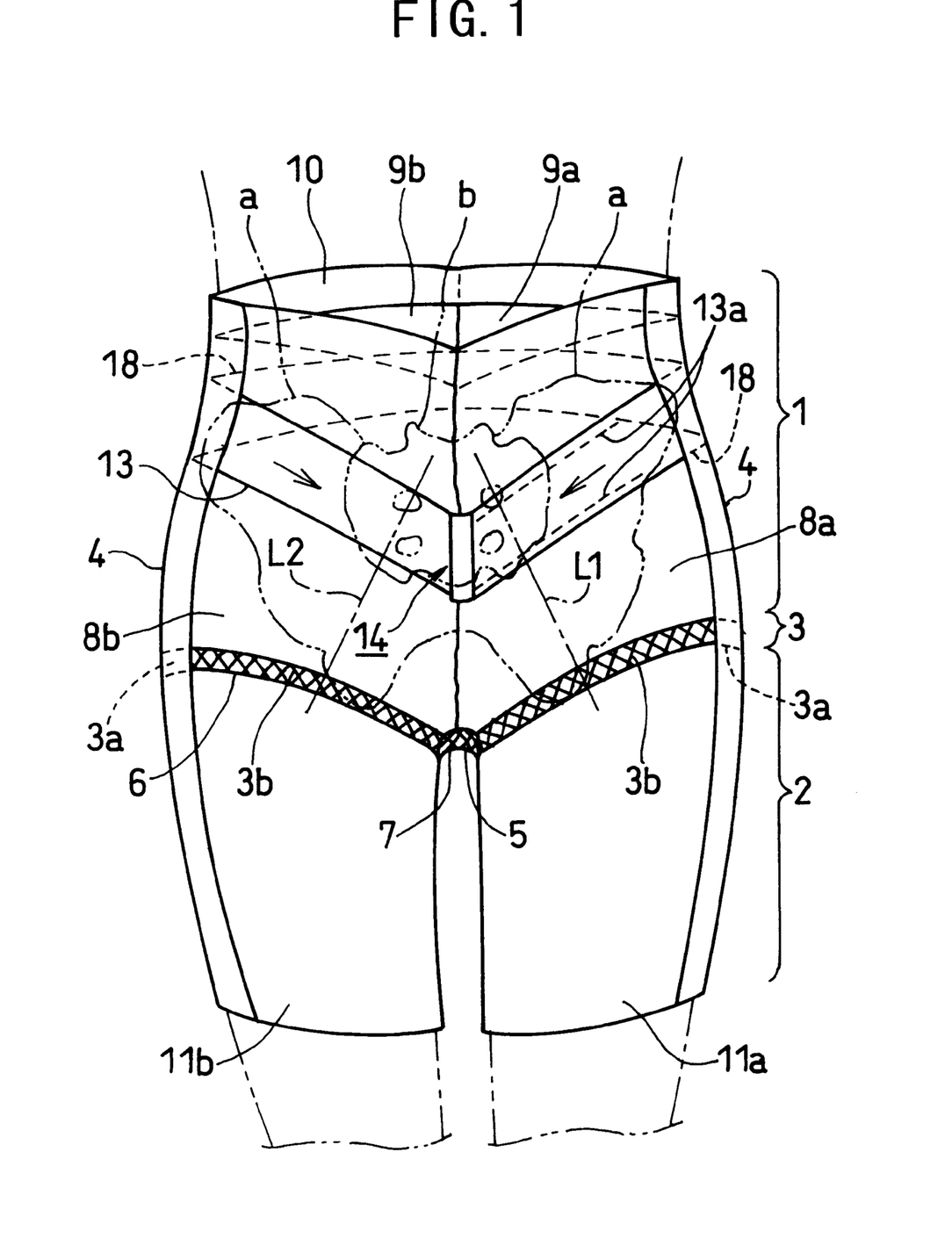
FIG. 1 is a front elevational view of the first embodiment of a panty girdle of the present invention.
Figure 2:
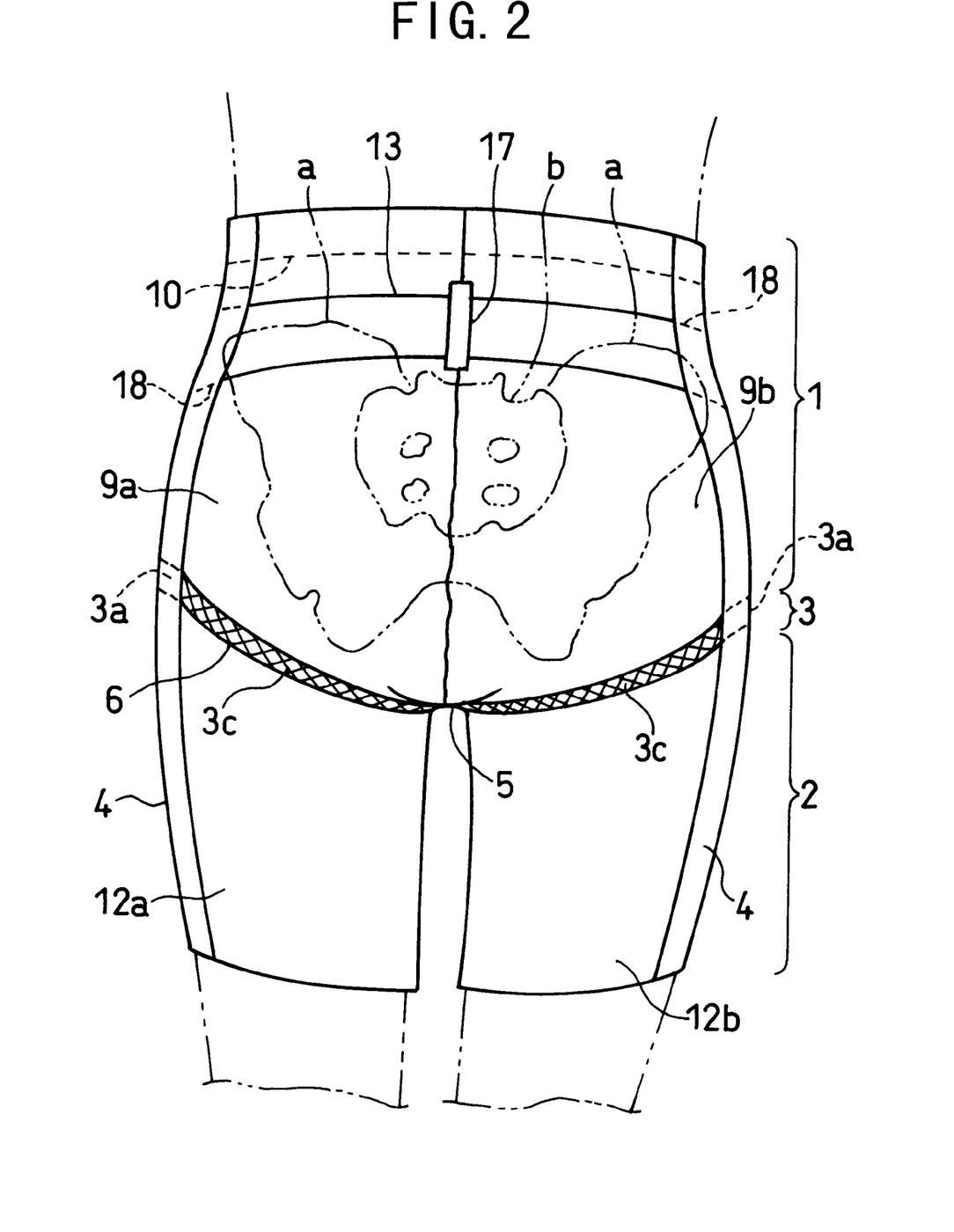
FIG. 2 is a rear elevational view thereof.
Figure 3:
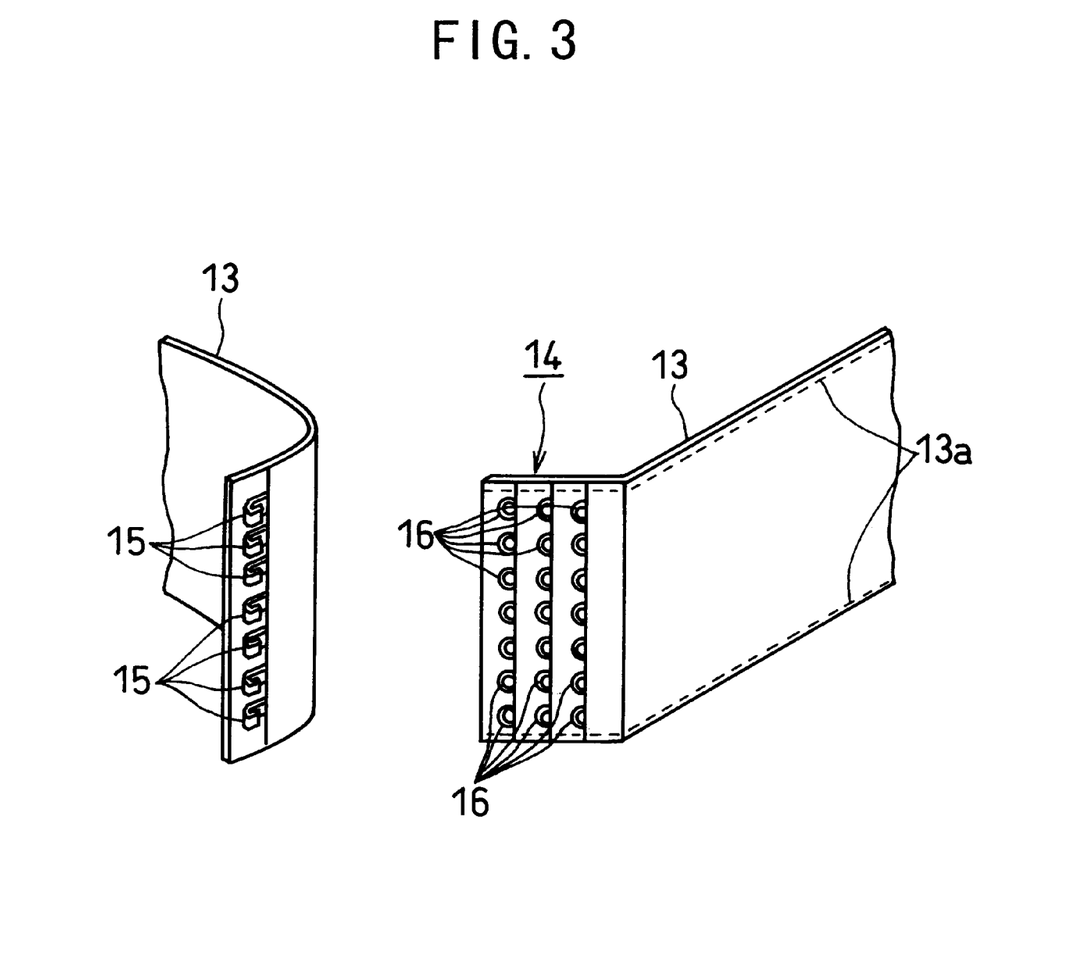
FIG. 3 is a perspective view of a connector for a belt.

FIGS. 1 to 3 illustrate the first embodiment of the present invention. Numeral 1 denotes a panty portion for covering the abdomen, buttocks and a lower back of a human body, and numeral 2 denotes a thigh covering portion which is connected with the panty portion via a hip joint portion 3.

Numeral 4 denotes a strong-net side cloth made from a bandshaped stretchable fibers having a certain width to provide strong shrinking force in vertical and horizontal directions, and is provided vertically over a side portion 3a of the hip joint portion 3 at the side of the panty portion 1 and the thigh covering portion 2.

Front and rear surfaces 3b and 3c of the hip joint portion 3 extend from a side portion 3a of the hip joint portion 3 to a lower middle portion 5 at which the thigh covering portion 2 is divided, and comprises a certain width of mesh tape 6 woven from stretchable fibers in bias form, having vertical and horizontal contracting force weaker than strong-net side cloth. The upper edge, the lower edge and outer side edge of each of the mesh tape 6 are sewn to the thigh portion 2, the strong-net side cloth 4 and lower middle portion 5 respectively. The connecting portion 5 is made of mesh material 7 which is the same as the mesh tape 6 or other air-permeable elastic material.

The panty portion 1 comprises two front panels 8a,8b made of non-elastic cloth such as silk, or less elastic lace cloth than the strong-net side cloth 4.

The panty portion 1 comprises two rear panels 9a,9b made of less elastic, thinner lace cloth than the front panels 8a,8b.

At the inner circumference of the upper end of the panty portion 1, an elastic band 10 is sewn to the upper ends of the strong-net side cloth 4, the front panels 8a,8b and the rear panels 9a,9b. Thus the upper portions of the strong-net side cloths 4, the front panels 8a,8b, the rear panels 9a,9b and the elastic band 10 constitutes the panty portion 1.

The thigh covering portion 2 comprises part of the strong-net side cloths 4, front panels 11a,11b which are made of the same material as that of the front panels 8a,8b, and rear panels 12a,12b, the upper ends of the front panels 11a,11b and the rear panels 12a,12b being sewn to the mesh tape 6 and the mesh material 7.

The foregoing structure is similar to what is disclosed in Japanese Utility Model Pub. No.4-21764, thereby making one's hip and thigh slenderer and flexion exercise easier, moving up fat of buttocks and thigh and preventing elevated fat from lowering gradually by flexion exercise.

In the embodiment of the present invention, it is added to the above structure that a belt 13 made of elastic material such as rubber, having higher elasticity than material of the front panels 8a,8b and rear panels 9a,9b, is attached across an upper part of the ilium of a wearer in the rear panels 9a,9b, and the belt 13 extends downwardly, both ends of the belt being connected in the middle of the front panels 8a,8b by a detachable connector 14 and attached to the panty portion 1.

The belt 13 is sewn to the left front panel 8a only at the left end. Numeral 13a denotes a sewn portion.

As shown in FIG. 3, the connector 14 comprises a plurality of hooks 15 at the right end of the belt 13, and a plurality of loops 16 in three rows at the left end of the belt 13 so that a row of the hooks 15 may be selectively engaged with any row of the loops 16 to adjust real circumference of the belt 13. The number of the hook and loop may be one respectively.

At the upper portion of the right and left rear panels 9b and 9a, there is provided a belt loop 17 through which the belt 13 is passed. In the strong-net side cloth 4 which meets the belt 13, there is formed a belt opening 18, into which the belt 13 is inserted. Therefore, as shown in FIG. 1, the right and left iliums "a" of the pelvis of the wearer are tightened in a direction of normal rotation which is almost the same as a direction for extending the belt 13 in the front panels 8a,8b to achieve normal pelvis correction.

That is to say, the tightening direction of the right and left iliums "a" by the belt 13 coincides with normal rotating direction of the iliums "a", and no gap therebetween is generated, thereby avoiding disadvantages to pelvis correction by stress to connecting portions of the iliums to the socrum or other bones (not shown) as disclosed in the prior art.

Figure 4:
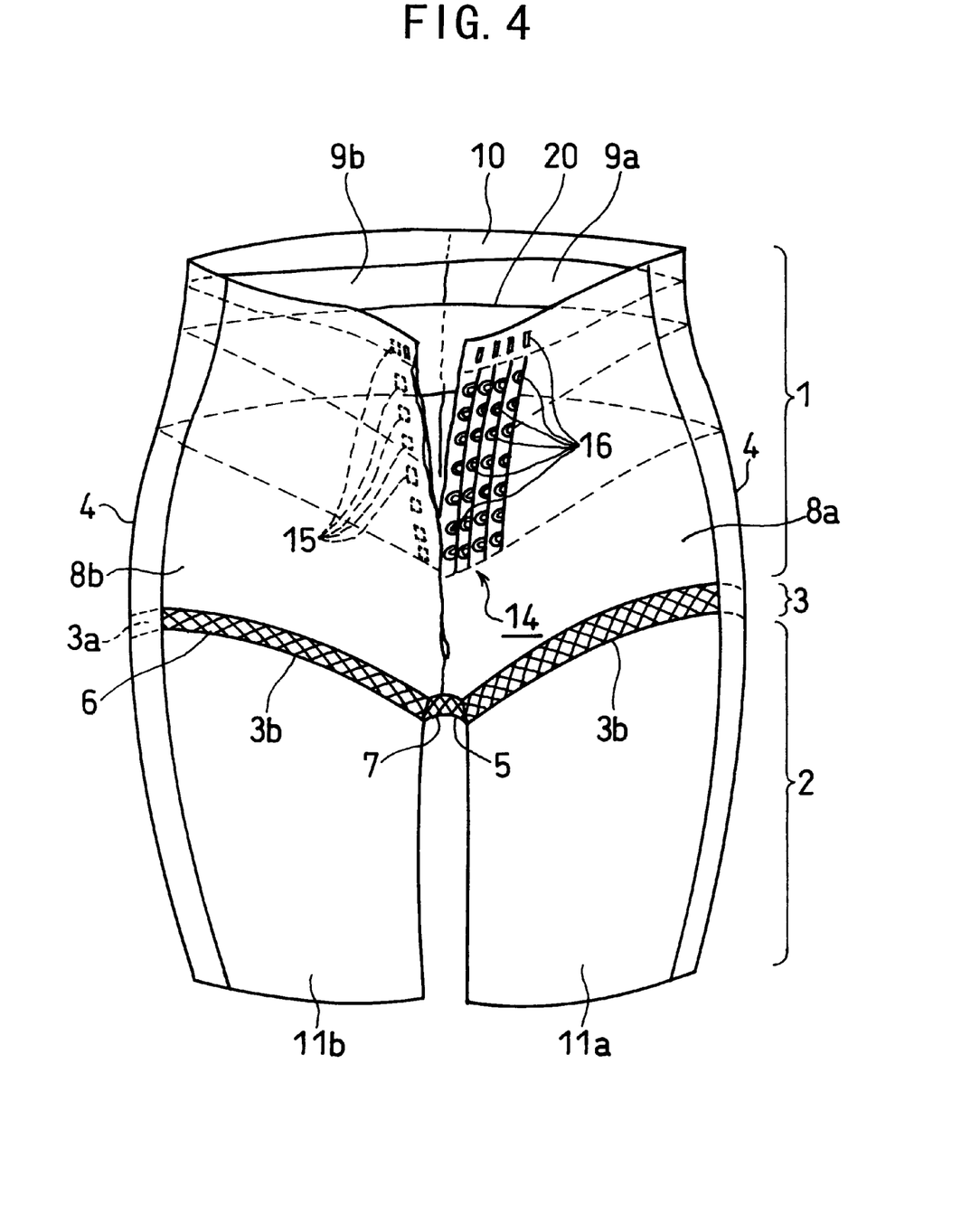
FIG. 4 is a front elevational view of the second embodiment of a panty girdle of the present invention.

FIG. 4 illustrates the second embodiment of the present invention, in which the same numerals are allotted to the same members as those in FIG. 1, and detailed description thereof is omitted.

In the second embodiment, a belt 20 wider than the belt 13 in the first embodiment is sewn to the inner circumferential surfaces of front panels 8a,8b and rear panels 9a,9b, and is opened between the right and left front panels 8a,8b. At the right front panel 8b, a plurality of hooks 15 similar to the above are provided and a plurality of rows of loops 16 are provided at the left front panel 8a. By engaging the hooks 15 with any row of the loops 16 selectively, the opening is closed and real circumference of the belt 20 can be adjusted. In the embodiment, the hooks 15 and the loops 16 constitute a connector 14 for the belt 20. In the second embodiment, similar advantages to the first embodiment can be achieved.

Figure 5:
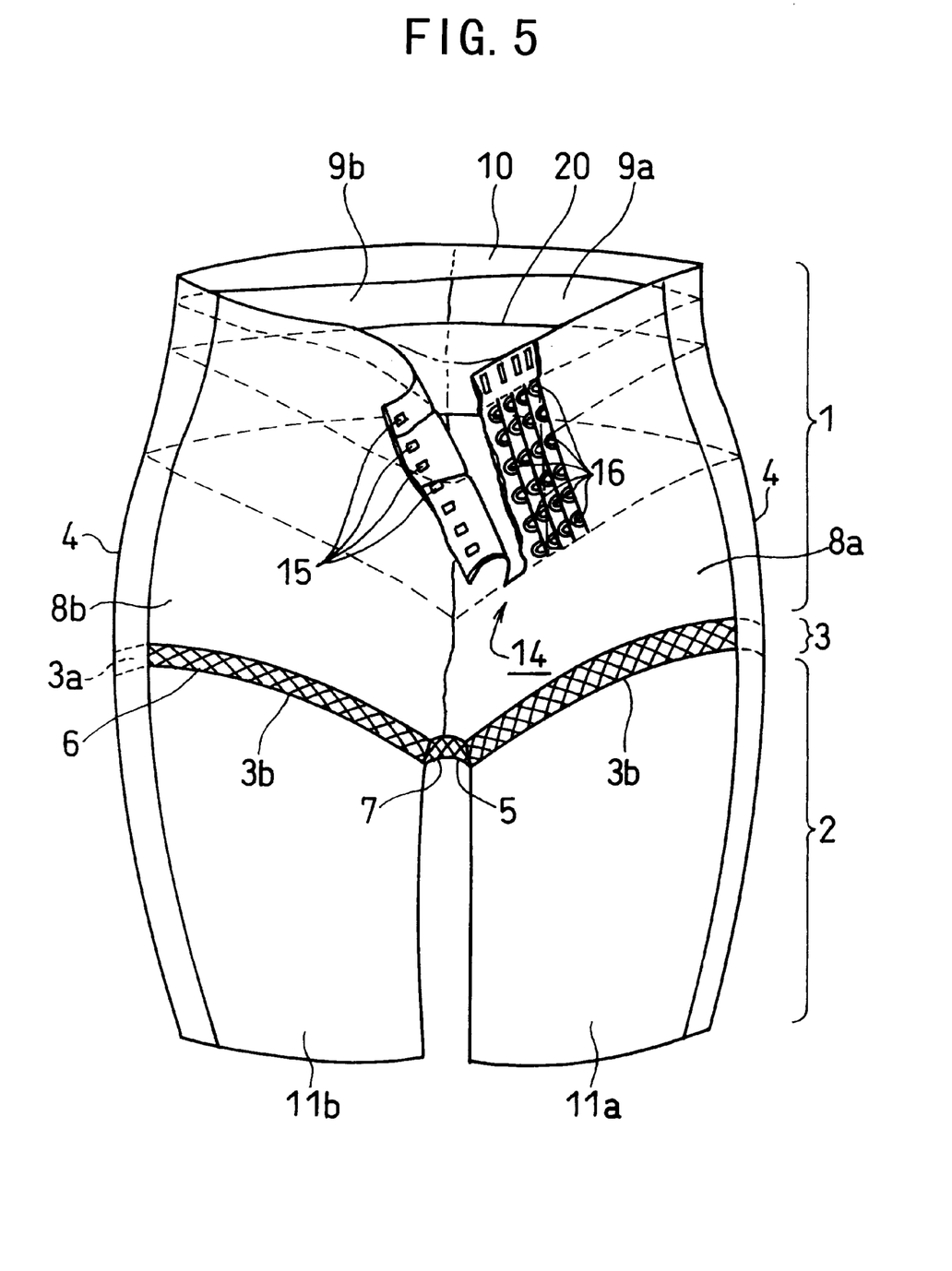
FIG. 5 is a front elevational view of the third embodiment of a panty girdle of the present invention.

FIG. 5 illustrates the third embodiment of the present invention, in which the belt 20 is sewn to the whole inner circumferential surface of the front panels 8a,8b and the rear panels 9a,9b. An opening is formed at the left front panel 8a. A plurality of hooks 15 are provided at the right front panel 8b, and a plurality of rows of loops 16 are provided at the left front panel 8b. By engaging the hooks 15 with any row of the loops 16 selectively, the opening is closed and real circumference of the belt 20 can be adjusted.

By engaging the hooks 15 with the loops 16, one side end can be overlapped on the other end obliquely. In this embodiment, the hooks 15 and the loops 16 act as a connector, and similar advantages to the first embodiment could be achieved.

Figure 6:
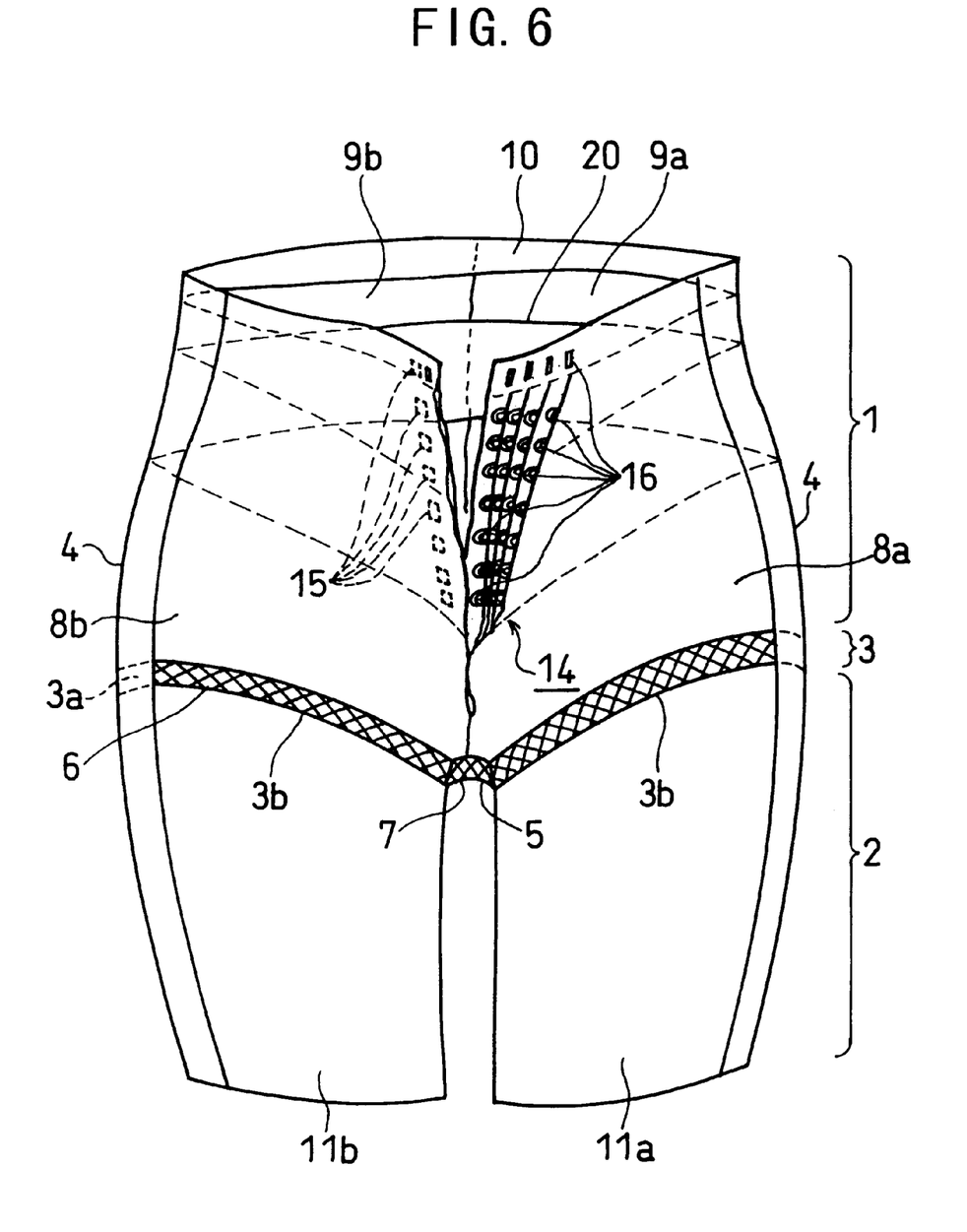
FIG. 6 is a front elevational view of the fourth embodiment of a panty girdle of the present invention.

FIG. 6 illustrates the fourth embodiment of the present invention. In this embodiment, a plurality of row of loops which are engaged with hooks 15 are arranged in V-shape in which its width becomes narrower downwards, so that an upper panty portion can be tightened depending on one's human body shape.

Figure 7:
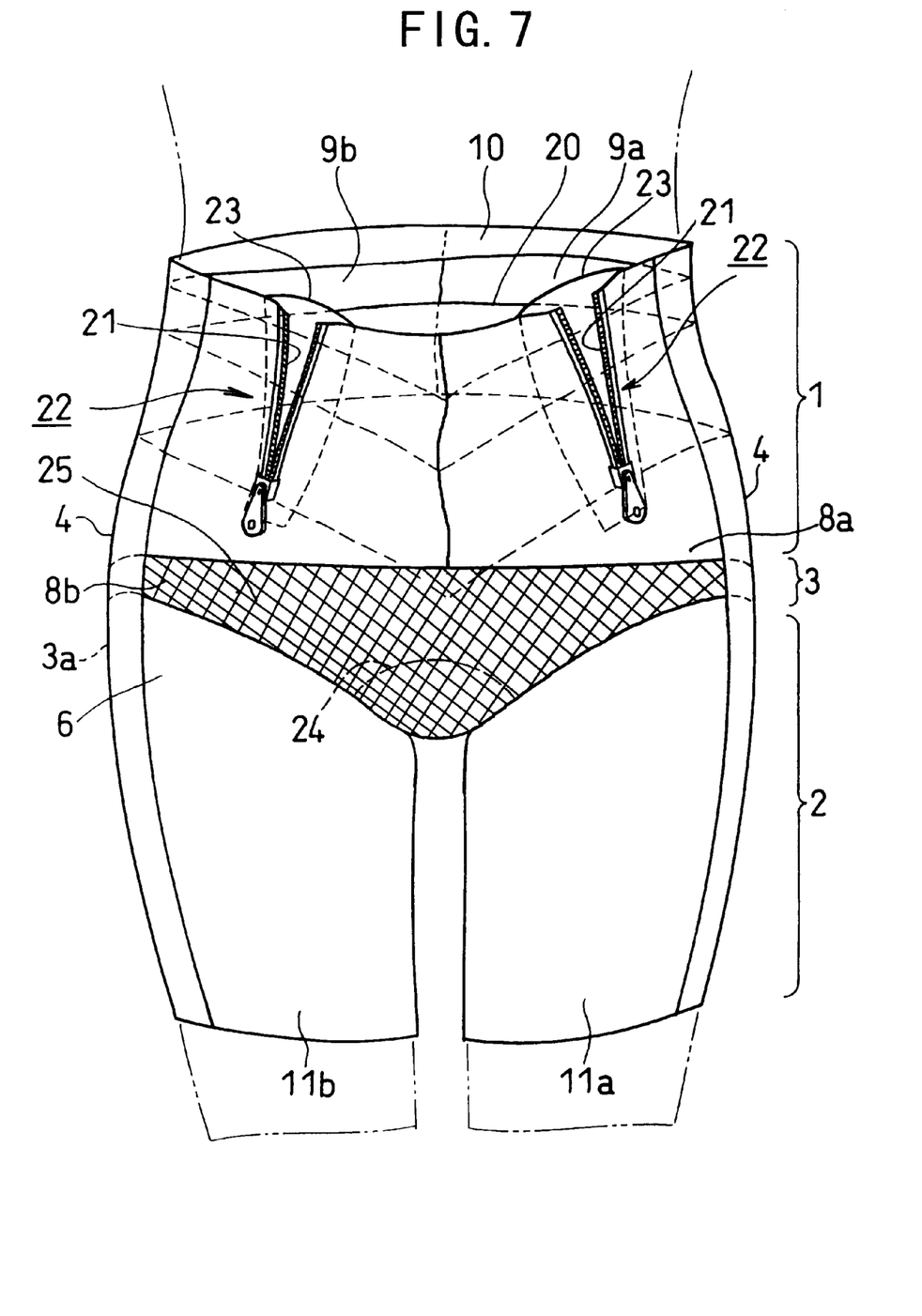
FIG. 7 is a front elevational view of the fifth embodiment of a panty girdle of the present invention.

FIG. 7 illustrates the fifth embodiment of the present invention, in which two cutaways 21 which extends perpendicular to a belt 20 are formed from the upper edges of front panels 8a,8b of a panty portion. The number of the cutaways 21 may be three. A known fastener 22 is provided at each of the cutaways 21. A V-shaped backing cloth 23 is sewn inside the fastener 22 of each of the front panels 8a,8b so that the cutaway 21 may be stretched as opened in V-shape.

A front half of the belt 20 is wholly or partially sewn to the inner surface of the backing cloths 23 and the front panels 8a,8b, A rear half of the belt 20 may be preferably sewn to the whole inner surface of the rear panels 9a,9b, but may be partially sewn.

The first to fourth embodiments are for female, but the fifth embodiment is for male, in which an opening 24 is formed in the lower middle of the front panels 8a,8b and is covered with a reversed triangular cover cloth 25 which is made of elastic mesh. Only the lower edge of the cloth 25 is sewn to the upper edge of a thigh covering portion 2. In the fifth embodiment, any of the fasteners 22 is opened to increase waist size stepwise and all the fasteners are opened and closed to allow a wearer to put on and off the panty girdle easily.

The cutaways 21 extends perpendicular to the belt 20, so that the front panels 8a,8b are tightened in the same direction as the belt 20 when the fasteners 22 are closed, thereby assisting tightening force of the belt 20 and improving normal pelvis correction effect.

Figure 8:
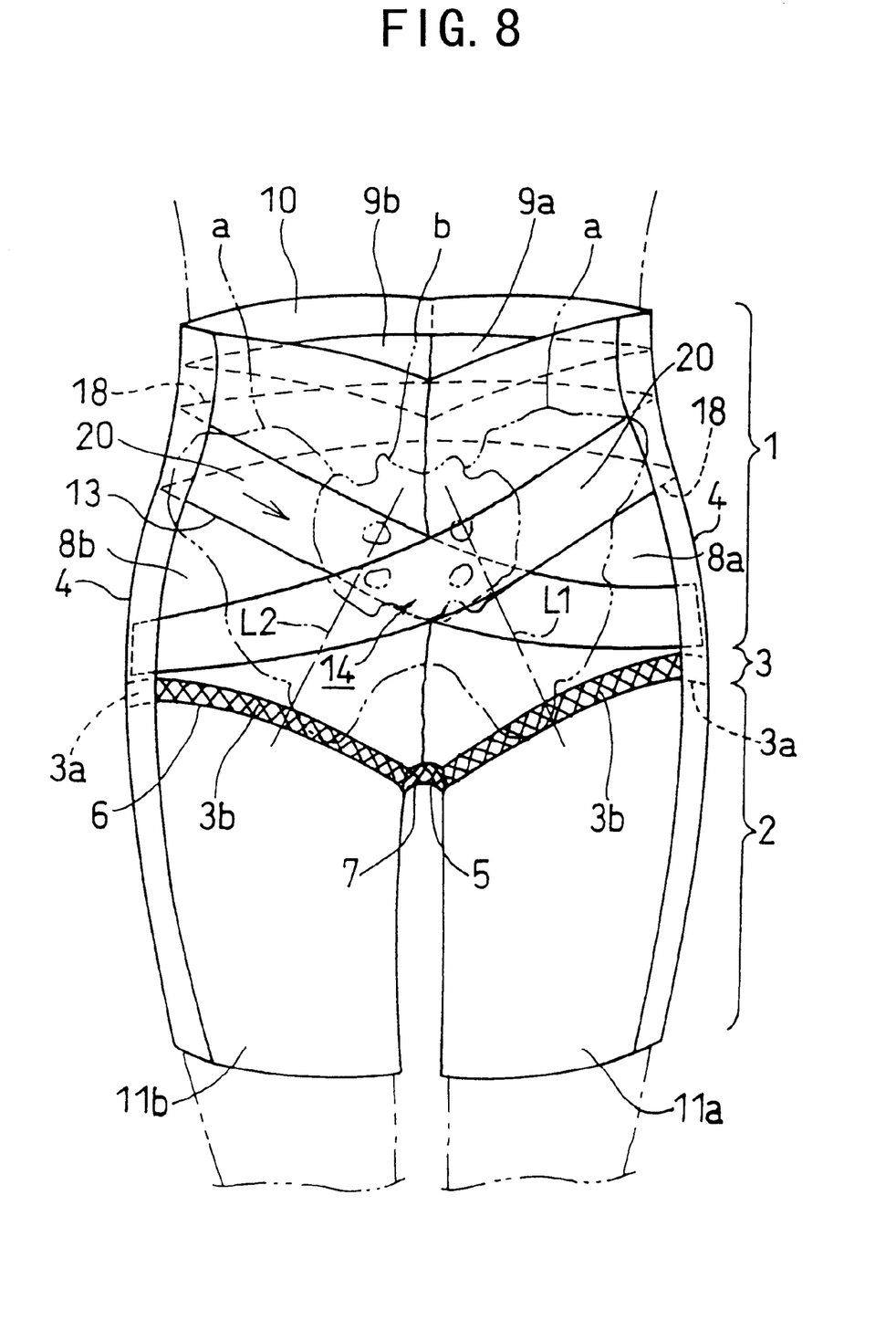
FIG. 8 is a front elevational view of the sixth embodiment of a panty girdle of the present invention.

FIG. 8 illustrates the sixth embodiment of the present invention, in which a belt 20 is crossed in the middle of front panels 8a,8b and the ends of the belt 20 extends to the side ends of a panty portion 1 and sewn to the inner surface of strong-net side cloths 4. The belt 20 extends to the side ends to increase tightening force of the belt 20 to improve pelvis correction effect. The belt 20 extends from the middle to the side ends downwards to prevent upward movement of the front panels 8a.8b.

Figure 9:
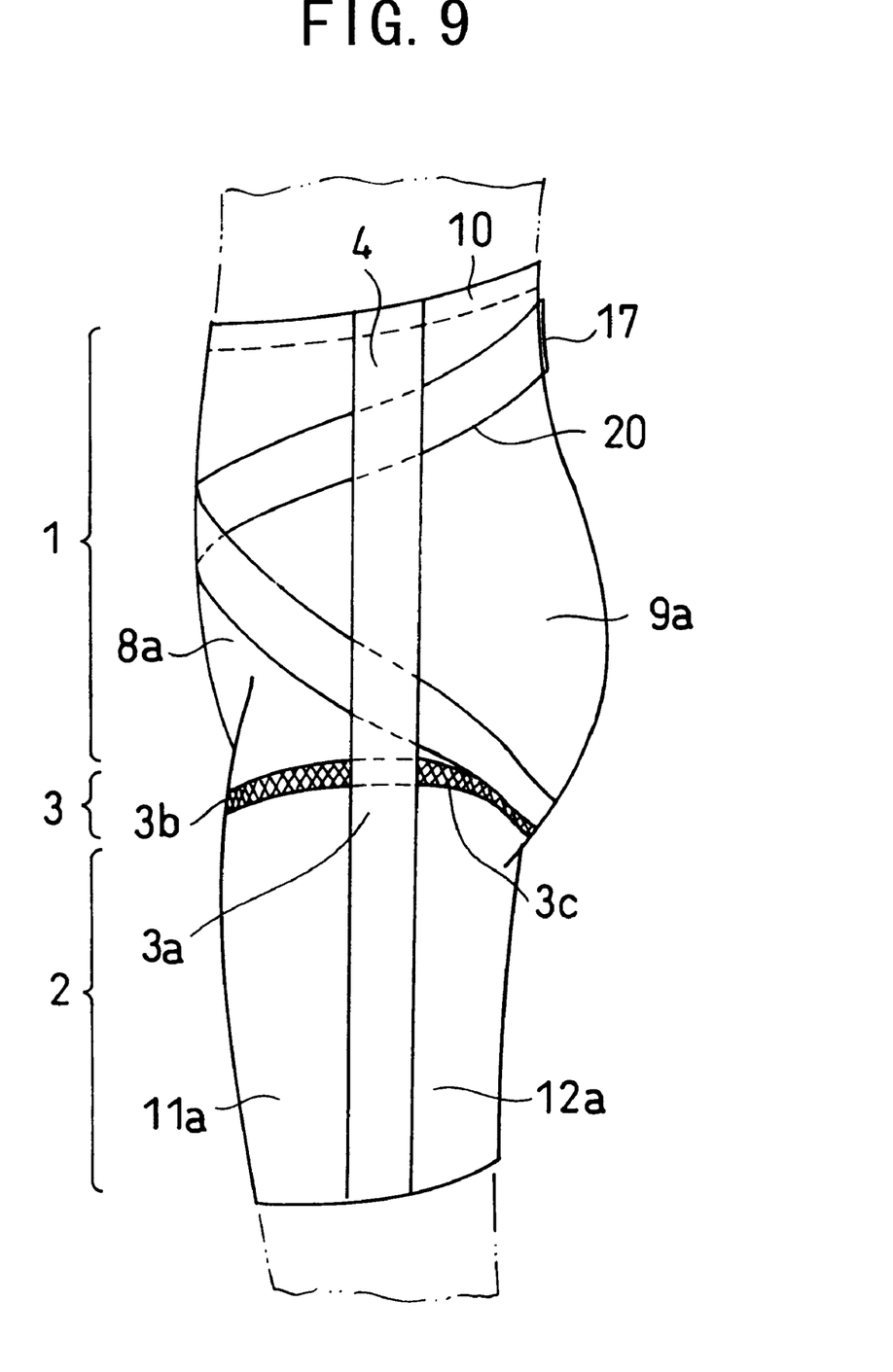
FIG. 9 is a side elevational view of the seventh embodiment of a panty girdle of the present invention.
Figure 10:
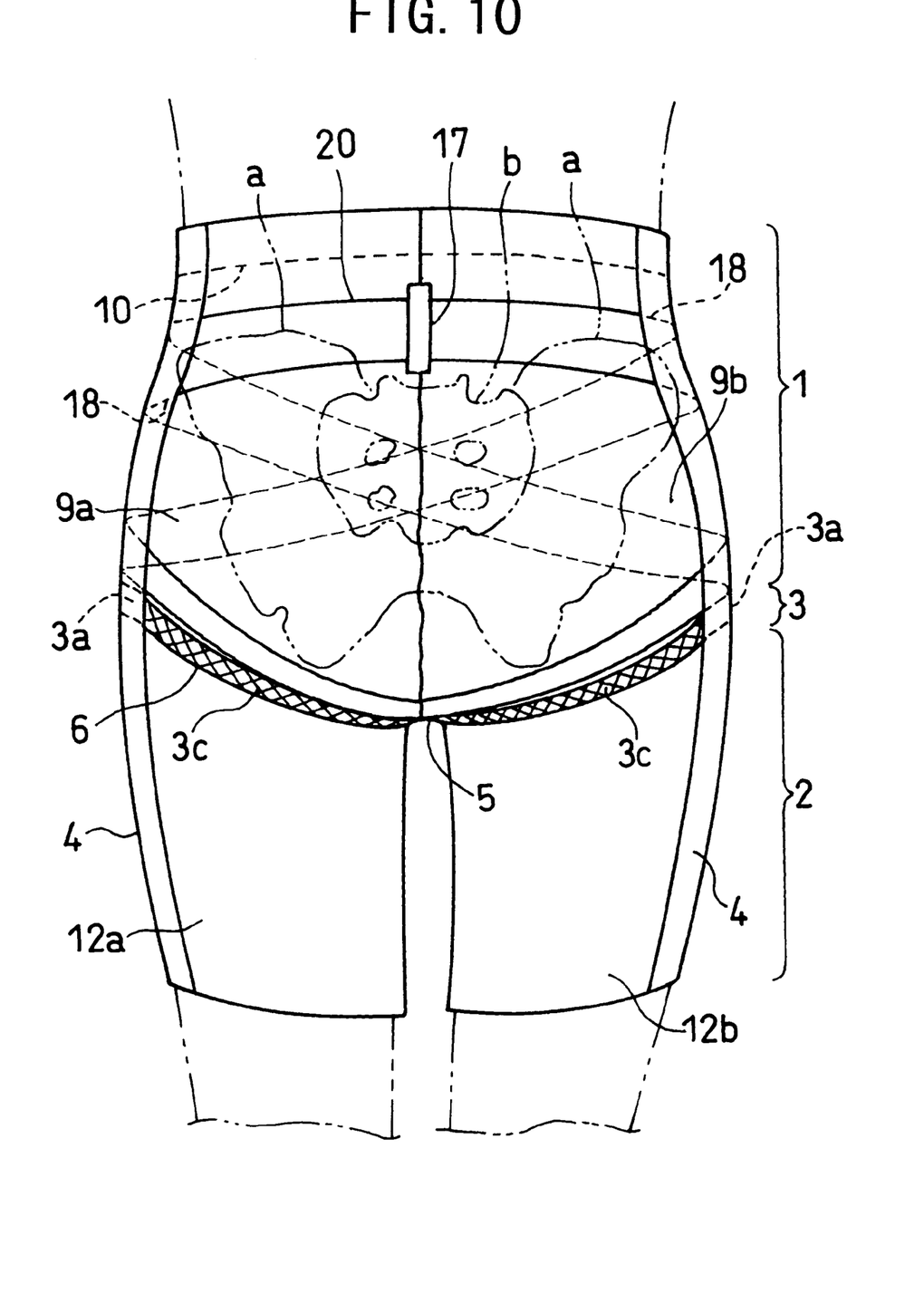
FIG. 10 is a back view of the same.

FIGS. 9 and 10 illustrate the seventh embodiment of the present invention, in which a belt 20 is crossed and extends to the lower middle part of rear panels 9a,9b where the ends of the belt 20 are connected to each other in the rear panels, so that the buttocks are raised.

The connector 14 in FIGS. 1 to 6 comprises the hooks 15 and the loops 16, but may be a known fastener or buckle. The belt 13 may be attached to a known panty girdle which has not strong-net side cloth or a mesh tape 5.

The foregoing merely relates to embodiments of the invention. Various changes and modifications may be made by person skilled in the art without departing from the scope of claims wherein:

What is claimed is:

1. A panty girdle which comprises:
   a panty portion which has right and left front panels for covering an abdomen and right and left rear panels for covering buttocks and a lower back, said front panels being connected by side portions and a lower middle portion to the rear panels;
   thigh covering portions for covering thighs; and
   a belt which is partially sewn to the panty girdle and extends circumferentially of the panty girdle, said belt being made of material more elastic than material of said front and rear panels, said belt extending downwards towards a middle of the front panels and horizontally in the rear panels at a position corresponding to upper portions of one's iliums to tighten one's iliums to make pelvis correction.

2. A panty girdle as defined in claim 1 wherein ends of said belt are connected by a connector at the middle of said front panels.

3. A panty girdle as defined in claim 1 wherein the panty portion is connected to the thigh covering portions by a mesh.

4. A panty girdle as defined in claim 2 wherein said connector comprises a plurality of hooks at one end of the belt and a plurality of rows of loops at the other end of the belt, said hooks being engaged with one of the rows of the loops.

5. A panty girdle as defined in claim 1 wherein the belt extends from the side portions towards a middle downwards in the front panels and horizontally in the rear panels, an opening being formed in a middle of the front panels, one side of the front panels having a plurality of hooks, the other side having a plurality rows of loops, said opening being closed by engaging the hooks with one of the rows of the loops.

6. A panty girdle as defined in claim 1 wherein the belt extends downwards towards a middle of the front panels and horizontally in the rear panels, an opening being formed at a position slightly deviated from a middle of the front panels perpendicular to a longitudinal direction of the belt of the front panels, said opening being closed by engaging the hooks with one of the rows of the loops.

7. A panty girdle as defined in claim 5 wherein said rows of the loops is converged downwards.

8. A panty girdle as defined in claim 1 wherein a cutaway is formed from an upper edge of the panty portion in a direction perpendicular to a longitudinal direction of the belt and closed by a fastener, a backing cloth being attached behind the fastener.

9. A panty girdle as defined in claim 8 wherein a small opening is formed at a lower middle between the thigh covering portions and covered with a mesh cloth so that the girdle may be used for males.

10. A panty girdle as defined in claim 1 wherein the belt which extends downwards towards a middle of the front panels is crossed and finally connected to the side portion.

11. A panty girdle as defined in claim 1 wherein the belt which extends downwards towards a middle of the front panels is crossed and finally connected to each other in the rear panels of the panty portion.

* * * * *